United States Patent [19]

Coronelli et al.

[11] 3,978,211

[45] Aug. 31, 1976

[54] LIPIARMYCIN AND ITS PREPARATION

[75] Inventors: Carolina Coronelli; Francesco Parenti, both of Milan; Richard White, Como; Hermes Pagani, Milan, all of Italy

[73] Assignee: Gruppo Lepetit S.p.A., Milan, Italy

[22] Filed: Oct. 31, 1974

[21] Appl. No.: 519,472

[30] Foreign Application Priority Data

Nov. 22, 1973 United Kingdom........... 54170/73

[52] U.S. Cl............................... 424/120; 195/80 R
[51] Int. Cl.².......................................... A61K 35/74
[58] Field of Search....................... 424/120; 195/80

[56] References Cited
OTHER PUBLICATIONS

Miller, The Pfizer Handbook of Microbial Metabolites, McGraw–Hill Book Co., Inc., N. Y., N. Y., 1961, p. 118.

Primary Examiner—Jerome D. Goldberg
Attorney, Agent, or Firm—Theodore Post; C. Kenneth Bjork

[57] ABSTRACT

The novel antibiotic, lipiarmycin, is prepared by cultivating *Actinoplanes deccanensis* A/10655, ATCC 21983, under aerobic conditions in a fermentation broth, from which it is then recovered.

3 Claims, 3 Drawing Figures

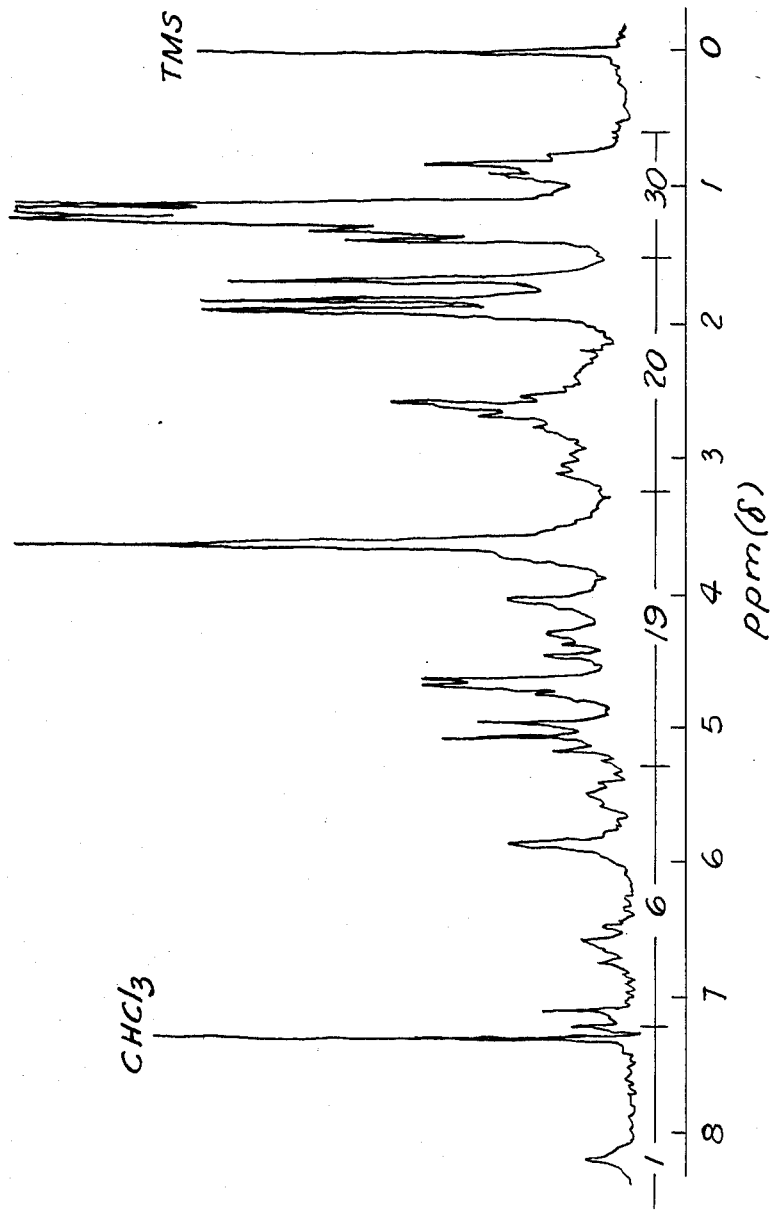

LIPIARMYCIN AND ITS PREPARATION

SUMMARY OF THE INVENTION

In the preparation of the novel antibiotic lipiarmycin, Actinoplanes deccanensis A/10655, which has been deposited and made part of the stock culture collection of ATCC, where it was assigned number 21983, is cultivated under aerobic conditions in an aqueous nutrient medium suitable for the growth of said organism, the medium containing a source of carbon, a source of nitrogen and inorganic salts. Ordinarily, the antibiotic-producing strain is pre-cultured in a shake flask until substantial antibiotic activity is present, then the culture is used to inoculate jar fermentors containing nutrient fermentative medium. Cultivation is continued at 25°-35°C under aerobic conditions for a time sufficient to produce a substantial antibiotic level. During this time, microbiological assays are carried out by the agar diffusion method to control the concentration of the antibiotic substance produced. The lipiarmycin is isolated from the fermentation broth by conventional procedures, such as, for instance, by extraction with an organic solvent in which the antibiotic substance is soluble and which is immiscible with the aqueous medium. Suitable organic solvents for such purpose are advantageously selected from halogenated $C_1$-$C_4$ hydrocarbons and $C_4$-$C_6$ alkanols. The solvent is then separated from the fermentation broth by high-speed centrifugation, concentrated to about 1/20-1/40 of its original volume and allowed to stand until the antibiotic substance precipitates.

The crude lipiarmycin is dissolved in a 90:10 chloroform:methanol mixture, chromatographed through a silica gel column and eluted with a mixture of chloroform and methanol in the same proportions as above. Lipiarmycin is finally crystallized from a mixture of diethyl ether and light petroleum.

DESCRIPTION OF THE PREFERRED EMBODIMENTS

Production of Lipiarmycin

Figure 1:
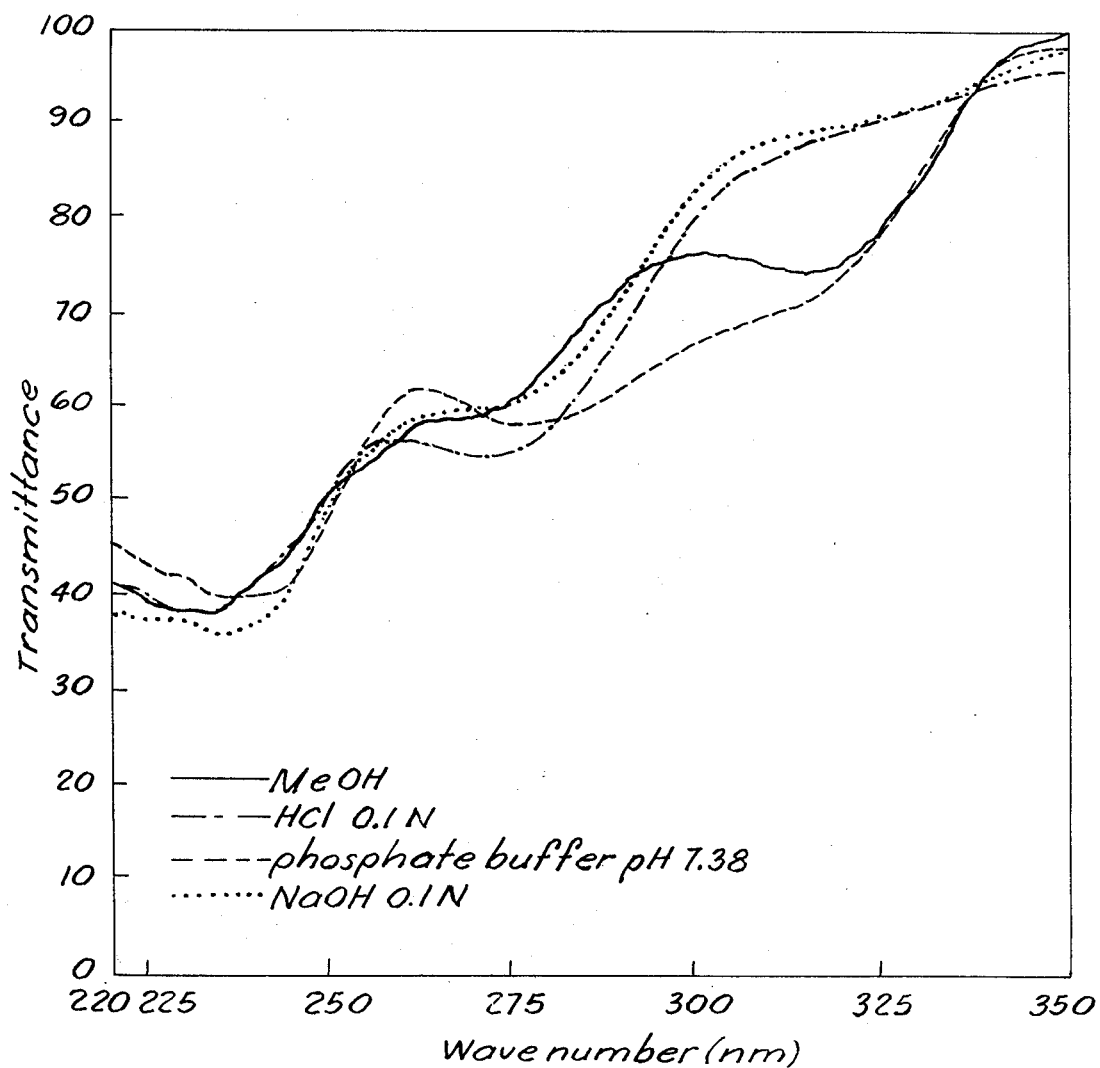

To produce the antibiotic lipiarmycin, the strain Actinoplanes deccanensis A/10655 is aerobically pre-cultured in a nutrient medium until substantial antibiotic activity is present at a pH value ranging from about 6 to about 8. As an example, a shake flask culture may have the following composition in g./l.

| | |
|---|---|
| Meat extract | 3.0 |
| Tryptone | 5.0 |
| Yeast extract | 5.0 |
| Glucose | 1.0 |
| Soluble starch | 24.0 |
| Calcium malate | 4.0 |
| Distilled water q.s. to | 1000 ml. |

The flasks are shaken for about 24 hours at about 28°-30°C., then the pre-cultures (one liter) are used to inoculate jar fermentors, each containing 10 liters of the following nutrient medium:

| | |
|---|---|
| Meat extract | 40 g. |
| Peptone | 40 g. |
| Yeast extract | 10 g. |
| Sodium chloride | 25 g. |
| Soybean meal | 100 g. |
| Glucose | 500 g. |
| Calcium carbonate | 50 g. |
| Tap water q.s. to | 10 liters |

The fermentation batches are incubated aerobically under stirring at 28°-30°C. At intervals, the antibiotic activity is assayed microbiologically by the agar diffusion method using Staphylococcus aureus as the test organism. The maximum activity is reached after 72-96 hours of fermentation.

Isolation of Lipiarmycin

When fermentation is completed the fermentation broth is extracted twice with an amount of butanol corresponding to 30 percent of its volume. The butanol solution is separated from the broth by high-speed centrifugation and is concentrated to about 1/20 of its original volume by evaporation under vacuum at 40°-50°C. The butanol solution so obtained is washed with water and the resulting two layers are separated. The organic layer is further concentrated to about 1/30 of its original volume and allowed to stand for about 3-7 hours at 4°C. until a precipitate forms, which is recovered by filtration. By addition of light petroleum to the filtrate, further crude compound is obtained. From 10 liters of fermentation broth, 11 g. of antibiotic substance are recovered.

The so obtained crude lipiarmycin is dissolved in a 90:10 chloroform:methanol mixture and to the resulting solution a compatible amount of silica gel is added. The mixture is evaporated to dryness under vacuum at 40°-50°C., the solid obtained is added to the top of a silica gel column and the subsequent elution is carried out with a mixture of chloroform and methanol in the same proportions as above.

The so obtained purified antibiotic is dissolved in a small amount of methanol and to the resulting solution is added diethyl ether and the resulting solution is heated to about 40°C. for a few minutes. Light petroleum is added to this warm solution until a slight opacity is observed, then the whole is allowed to stand at 3°-6°C. for one day. Pure lipiarmycin thereby precipitates, which is recovered by filtration and dried under vacuum.

Lipiarmycin as so produced is a white crystalline substance having the following properties:

1. Melting point: 173°-75°C. (from a mixture of methanol, diethyl ether and light petroleum)
2. Molecular weight: 1076 (potentiometric determination)
3. Elemental analysis: C 58.02%; H 6.94%; Cl 6.64%; O 28.40% (by difference)
4. U.V. absorption bands In each of the below-outlined solvent systems, lipiarmycin shows the following values:

| Solvent | max (m $\mu$) | $E_{1\,cm.}^{1\%}$ |
|---|---|---|
| methanol | 232 | 354 |
| | 268 (shoulder) | 214 |
| | 315 | 108 |
| phosphate buffer pH 7.38 | 238 | 331 |
| | 275 | 194 |
| hydrochloric acid 0.1 N | 231 | 338 |
| | 272 | 207 |
| sodium hydroxide 0.1 N | 235 | 370 |

-continued

| Solvent | max (m μ) | $E_{1\ cm}^{1\%}$ |
|---|---|---|
| | 270 (shoulder) | 183 |

The complete picture of the spectrum is given in accompanying FIG. 1.

5. Infrared Spectrum

Characteristic absorption bands occur at the following frequencies (cm.$^{-1}$): 3600, 3450, 2900(Nujol), 1730, 1690, 1640, 1585, 1560, 1460(Nujol), 1380(Nujol), 1300, 1240, 1200, 1140, 1120, 1075, 1025, 990, 950, 915, 900, 890, 850, 820, 790, 780, 745, 720, 705.

Figure 2:
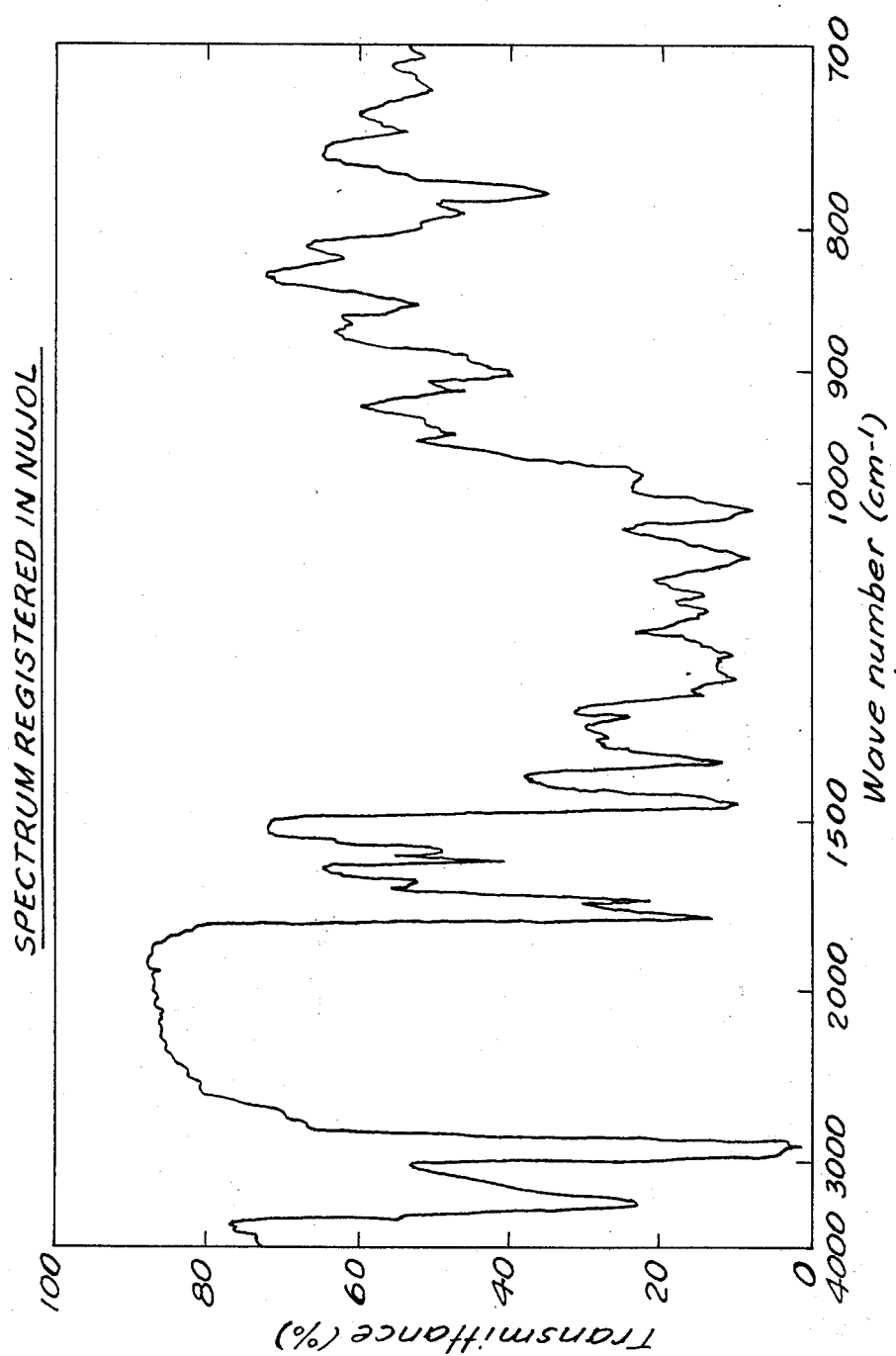

A complete figure of the I.R. spectrum is given in accompanying FIG. 2.

6. Specific rotation: $[\alpha]_D^{20}$ (1.98 percent methanol) $= -5.5°$

7. Proton Magnetic Resonance (P.M.R.) spectrum: see accompanying FIG. 3.

8. Solubility

Very soluble in ethanol, methanol, pyridine, aqueous sodium carbonate.

Fairly soluble in benzene, methylene chloride, chloroform, acetone, propanol.

Sparingly soluble to insoluble in water, buffered solution at pH 7, aqueous sodium bicarbonate, hexane.

9. Characteristic reactions

| Tollens | positive |
|---|---|
| FeCl$_3$ | positive |
| H$_2$SO$_4$ | positive |
| Schiff | negative |
| Millon | negative |
| Maltole | negative |

10. Acidity

An ionizable function is spectrophotometrically evidenced with pKa (in methyl cellosolve): 6.8

On the basis of microanalytical data, lipiarmycin may be assigned the following empirical formula: $C_{52}H_{74}Cl_2O_{19}$.

The antibiotic substance of the invention is active against bacteria, and in particular against the following microorganisms at the indicated concentrations.

| STRAIN | MINIMAL INHIBITORY CONCENTRATION γ/ml. |
|---|---|
| Staphylococcus aureus ATCC 6538 | 2 |
| Staphylococcus aureus Tour | 2 |
| Streptococcus hemolyticus C203 | 10 |
| Diplococcus pneumoniae UC 41 | 50 |
| Staphylococcus aureus Tour with 10 percent bovine serum | 10 |
| Streptococcus mutans ATCC 25175 | 0.5 |
| Mycobacterium tub. H37Rv ATCC 9360 | 50 |
| Mycoplasma gallisepticum H 21 C.Z.B. | 50 |

Lipiarmycin is also active against strains which are resistant to other antibiotics which are widely used in chemotherapeutic practice. As a representative example, in the following table the minimum inhibitory concentrations (M.I.C.), γ/ml., of lipiarmycin against Staphylococcus aureus strains resistant to several antibiotics are reported.

Table II

| STRAIN | M.I.C. of other antibiotics | M.I.C. of lipiarmycin |
|---|---|---|
| Staphylococcus aureus ATCC 6538 resistant to penicillin | penicillin >100 | 2 |
| Staphylococcus aureus ATCC 6538 resistant to streptomycin | streptomycin >100 | 5 |
| Staphylococcus aureus ATCC 6538 resistant to tetracycline | tetracycline >100 | 5 |
| Staphylococcus aureus ATCC 6538 resistant to novobiocin | novobiocin >100 | 2 |
| Staphylococcus aureus ATCC 6538 resistant to neomycin | neomycin >100 | 2 |
| Staphylococcus aureus ATCC 6538 resistant to erythromycin | erythromycin >100 | 5 |
| Staphylococcus aureus ATCC 6538 resistant to chloramphenicol | chloramphenicol >100 | 2 |
| Staphylococcus aureus ATCC 6538 resistant to cephaloridine | cephaloridine >100 | 5 |
| Staphylococcus aureus ATCC 6538 resistant to streptothricin | streptothricin >100 | 5 |
| Staphylococcus aureus ATCC 6538 resistant to bacitracin | bacitracin >100 | 5 |
| Staphylococcus aureus ATCC 6538 resistant to oleandomycin | oleandomycin 50 | 5 |

These favorable antimicrobial properties are coupled with a very low toxicity, the LD$_{50}$ value of lipiarmycin being about 500 mg./kg. i.p. in mice. Accordingly, the present invention provides a therapeutic composition comprising the compound of the invention together with a pharmaceutically-acceptable carrier.

Description of *Actinoplanes deccanensis* A/10655

This strain grows well on many agars. The surface is opaque and slightly rough to wrinkled. Aerial mycelium is always absent. At microscopic examination the vegetative mycelium is branched, with a diameter of about 1 μ. The sporangia form abundantly on soil extract agar and are globose with an irregular surface and a diameter ranging from 4–7 μ. After rupture of the wall of the sporangium, it is possible to observe spore release. The spores are sub-spherical and are motile (size 1 μ × 1.5 μ).

Table III reports the cultural characteristics of *Actinoplanes deccanensis* A/10655 when cultivated on various standard media suggested by Shirling and Gottlieb (Intern. J. Syst. Bact., 16, 313–340, 1966) and other media recommended by Waksman (The Actinomycetes, vol. II, The Williams and Wilkins Co., 1961). The cultural characteristics were determined after 6 to 14 days of incubation at 30°C.

Table III

The numbers of some of the culture media refer to those given by Shirling and Gottlieb.

| Culture Media | Cultural Characteristics |
|---|---|
| Medium No. 2 (yeast extract-malt agar) | Abundant growth, very wrinkled, light orange |
| Medium No. 3 (Oatmeal agar) | Moderate growth, crusty, light amber |
| Medium No. 4 (Inorganic salts-starch agar) | Abundant growth, crusty, orange |
| Medium No. 5 (Glycerol-asparagine agar) | Moderate growth, rough surface, orange |
| Medium No. 6 (Peptone-yeast extract-iron agar) | Moderate growth, wrinkled, light orange |

Table III-continued

The numbers of some of the culture media refer to those given by Shirling and Gottlieb.

| Culture Media | Cultural Characteristics |
| --- | --- |
| Medium No. 7 (Tyrosine agar) | Abundant growth, wrinkled, amber to light brown, diffusible brown, pigment |
| Oatmeal agar according to Waksman | Abundant growth, crusty, opaque, light orange |
| Hickey and Tresner's agar | Abundant growth, wrinkled, light orange-pinkish |
| Czapeck glucose agar | Moderate growth, crusty, cream to light orange |
| Glucose asparagine agar | Moderate growth, slightly crusty, opaque, cream to light orange |
| Nutrient agar | Moderate growth, crusty, opaque, light orange |
| Potato agar | Abundant growth, very wrinkled, pale orange |
| Bennett's agar | Abundant growth, wrinkled, light orange |
| Calcium malate agar | Scanty growth, wrinkled, opaque light orange |
| Skim milk agar | Abundant growth, wrinkled, opaque orange |
| Czapeck agar | Moderate growth, crusty, light orange |
| Egg agar | Scanty growth, thin, opaque, white-waxy |
| Peptone glucose agar | Moderate growth, crusty, orange |
| Agar | Very scant growth, thin, hyaline |
| Loeffler serum | Moderate growth, rough surface, orange |
| Potato | Moderate growth, wrinkled, light orange |
| Gelatin | Scanty growth, light orange |
| Cellulose agar | Very scanty growth, thin, hyaline |

The most convenient temperature for development of the colonies was found to range from about 18° to about 42°C.; the optimum temperature being from about 28° to about 37°C.

Table IV reports the utilization of carbon sources examined according to the method of Pridham and Gottlieb.

Table IV

| Carbon sources | Utilization |
| --- | --- |
| Inositol | − |
| Fructose | − |
| Rhamnose | + |
| Mannitol | − |
| Xylose | + |
| Raffinose | − |
| Arabinose | + |
| Cellulose | − |
| Sucrose | + |
| Glucose | + |
| Mannose | + |
| Lactose | + |
| Salicin | − |

Following Table V reports the physiological characteristics of the strain.

Table V

| TEST | RESULTS |
| --- | --- |
| Hydrolysis of starch | positive |
| H₂S formation | negative |
| Tyrosinase reaction | positive |
| Casein hydrolysis | negative |
| Solubilization of calcium malate | positive |
| Nitrate reduction | positive |
| Liquefaction of gelatine | positive |
| Litmus milk coagulation | negative |
| Litmus milk peptonization | negative |
| Cellulose decomposition | negative |
| Chromogenic action | positive |

What is claimed is:

1. An antibiotic named lipiarmycin having the following characteristics:
   a. Melting point: 173°–175°C.
   b. Molecular weight (potentiometric determination): 1076
   c. Elemental analysis: C: 58.02%; H: 6.94%; Cl: 6.64%; O: 28.40% (by difference);
   d. Characteristic U.V. absorption bands in the following solvent systems:

| Solvent | max(m $\mu$) | $E_{1\ cm.}^{1\%}$ |
| --- | --- | --- |
| methanol | 232 | 354 |
|  | 268 (shoulder) | 214 |
|  | 315 | 108 |
| phosphate buffer pH 7.38 | 238 | 331 |
|  | 275 | 194 |
| hydrochloric acid 0.1 N | 231 | 338 |
|  | 272 | 207 |
| sodium hydroxide 0.1 N | 235 | 370 |
|  | 270 (shoulder) | 183 | e. Characteristic infrared absorption bands in Nujol at the following frequencies (cm. $^{-1}$): 3600, 3450, 2900(Nujol), 1730, 1690, 1640, 1585, 1560, 1460(Nujol), 1380(Nujol), 1300, 1240, 1200, 1140, 1120, 1075, 1025, 990, 950, 915, 900, 890, 850, 820, 790, 780, 745, 720, 705
   f. Specific rotation $[\alpha]_D^{20}$ (1.98% methanol)=−5.5°
   g. Solubility:
      Very soluble in methanol, ethanol, pyridine, aqueous sodium carbonate;
      Fairly soluble in benzene, methylene chloride, chloroform, acetone, propanol;
      Sparingly soluble to insoluble in water, buffered solution at pH 7, aqueous sodium bicarbonate, hexane
   h. Characteristic reactions:
      Tollens: positive
      FeCl₃: positive
      H₂SO₄: positive
      Schiff: negative
      Millon: negative
      Maltole: negative
   i. pKa in methylcellosolve:6.8

2. A process for producing the antibiotic lipiarmycin which comprises aerobically cultivating the microorganism Actinoplanes deccanensis A/10655, ATCC 21983, in an aqueous nutrient medium containing assimilable sources of carbon, nitrogen and inorganic salts and recovering therefrom lipiarmycin formed during the culture.

3. A culture containing the microorganism strain Actinoplanes deccanensis ATCC 21983, said culture being capable of producing the antibiotic lipiarmycin in a recoverable quantity upon aerobic fermentation in an aqueous nutrient medium containing assimilable sources of carbon, nitrogen and inorganic salts.

* * * * *

UNITED STATES PATENT AND TRADEMARK OFFICE
CERTIFICATE OF CORRECTION

PATENT NO. : 3,978,211
DATED : August 31, 1976
INVENTOR(S) : Carolina Coronelli et al.

It is certified that error appears in the above-identified patent and that said Letters Patent are hereby corrected as shown below:

Column 6, Claims 2 and 3, lines 54 through 66, should read as follows:

2. A process for producing the antibiotic lipiarmycin which comprises aerobically cultivating the microorganism Actinoplanes deccanensis A/10655, ATCC 21983, in an aqueous nutrient medium containing assimilable sources of carbon, nitrogen and inorganic salts until substantial antibiotic activity is imparted to said medium and recovering therefrom lipiarmycin formed during the culture.

3. A culture consisting essentially of the microorganism strain Actinoplanes deccanensis ATCC 21983 and an aqueous nutrient culture medium containing assimilable sources of carbon, nitrogen and inorganic salts, said culture being capable of producing the antibiotic lipiarmycin in a recoverable quantity upon aerobic fermentation.

Signed and Sealed this

Seventeenth Day of May 1977

[SEAL]

Attest:

RUTH C. MASON
Attesting Officer

C. MARSHALL DANN
Commissioner of Patents and Trademarks